US012629280B2

(12) United States Patent
Figueiredo Pereira et al.

(10) Patent No.: US 12,629,280 B2
(45) Date of Patent: May 19, 2026

(54) IMPLANTABLE OCULAR DRAINAGE DEVICE FOR CONTROLLING INTRAOCULAR PRESSURE

(71) Applicants: UNIVERSITEIT MAASTRICHT, Maastricht (NL); ACADEMISCH ZIEKENHUIS MAASTRICHT, Maastricht (NL); TECHNISCHE UNIVERSITEIT EINDHOVEN, Eindhoven (NL)

(72) Inventors: Inês Carolina Figueiredo Pereira, Eindhoven (NL); Rosanne Francisca Van De Wijdeven, Eindhoven (NL); Sebastian Fredrich, Eindhoven (NL); Albertus Petrus Hendricus Johannes Schenning, Eindhoven (NL); Hans Markus Wyss, Eindhoven (NL); Helena Jacqueline Maria Beckers, Eijsden (NL); Jacob Marinus Jan Den Toonder, Eindhoven (NL)

(73) Assignees: UNIVERSITEIT MAASTRICHT, Maastricht (NL); ACADEMISCH ZIEKENHUIS MAASTRICHT, Maastricht (NL); TECHNISCHE UNIVERSITEIT, Eindhoven (NL)

( * ) Notice: Subject to any disclaimer, the term of this patent is extended or adjusted under 35 U.S.C. 154(b) by 448 days.

(21) Appl. No.: 18/254,133

(22) PCT Filed: Oct. 5, 2021

(86) PCT No.: PCT/EP2021/077459
§ 371 (c)(1),
(2) Date: May 23, 2023

(87) PCT Pub. No.: WO2022/111892
PCT Pub. Date: Jun. 2, 2022

(65) Prior Publication Data
US 2024/0091062 A1 Mar. 21, 2024

(30) Foreign Application Priority Data

Nov. 30, 2020 (EP) ...................................... 20210723

(51) Int. Cl.
*A61F 9/007* (2006.01)

(52) U.S. Cl.
CPC .............................. *A61F 9/00781* (2013.01)

(58) Field of Classification Search
CPC ................................................... A61F 9/00781
See application file for complete search history.

(56) References Cited

U.S. PATENT DOCUMENTS

2011/0071456 A1    3/2011  Rickard
2015/0057596 A1*   2/2015  Lind ................... A61F 9/00781
                                                                 604/9

(Continued)

FOREIGN PATENT DOCUMENTS

JP     2011-504392 A     2/2011
WO     WO2019/051475 A1  3/2014

OTHER PUBLICATIONS

International Search Report for International Application No. PCT/EP2021/077459, mailed Oct. 1, 2022, 3 pages.

(Continued)

*Primary Examiner* — Susan S Su
*Assistant Examiner* — Erin A Kim
(74) *Attorney, Agent, or Firm* — TraskBritt

(57) ABSTRACT

The disclosure relates to an implantable ocular drainage device for controlling intraocular pressure (IOP) comprising at least one drainage channel, and at least one magnetic control mechanism. The at least one magnetic control mechanism is a magnetic valve mechanism configured to regulate flow in the at least one drainage channel.

14 Claims, 6 Drawing Sheets

(56) References Cited

U.S. PATENT DOCUMENTS

2015/0257930 A1    9/2015  Lind
2020/0276050 A1 *  9/2020  Simons ............... A61F 9/00781

OTHER PUBLICATIONS

International Written Opinion for International Application No. PCT/EP2021/077459, mailed Oct. 1, 2022, 5 pages.
Japanese Notice of Reasons for Refusal for Japanese Application No. 2023-531633, dated Nov. 11, 2025, 7 pages with English translation.

* cited by examiner

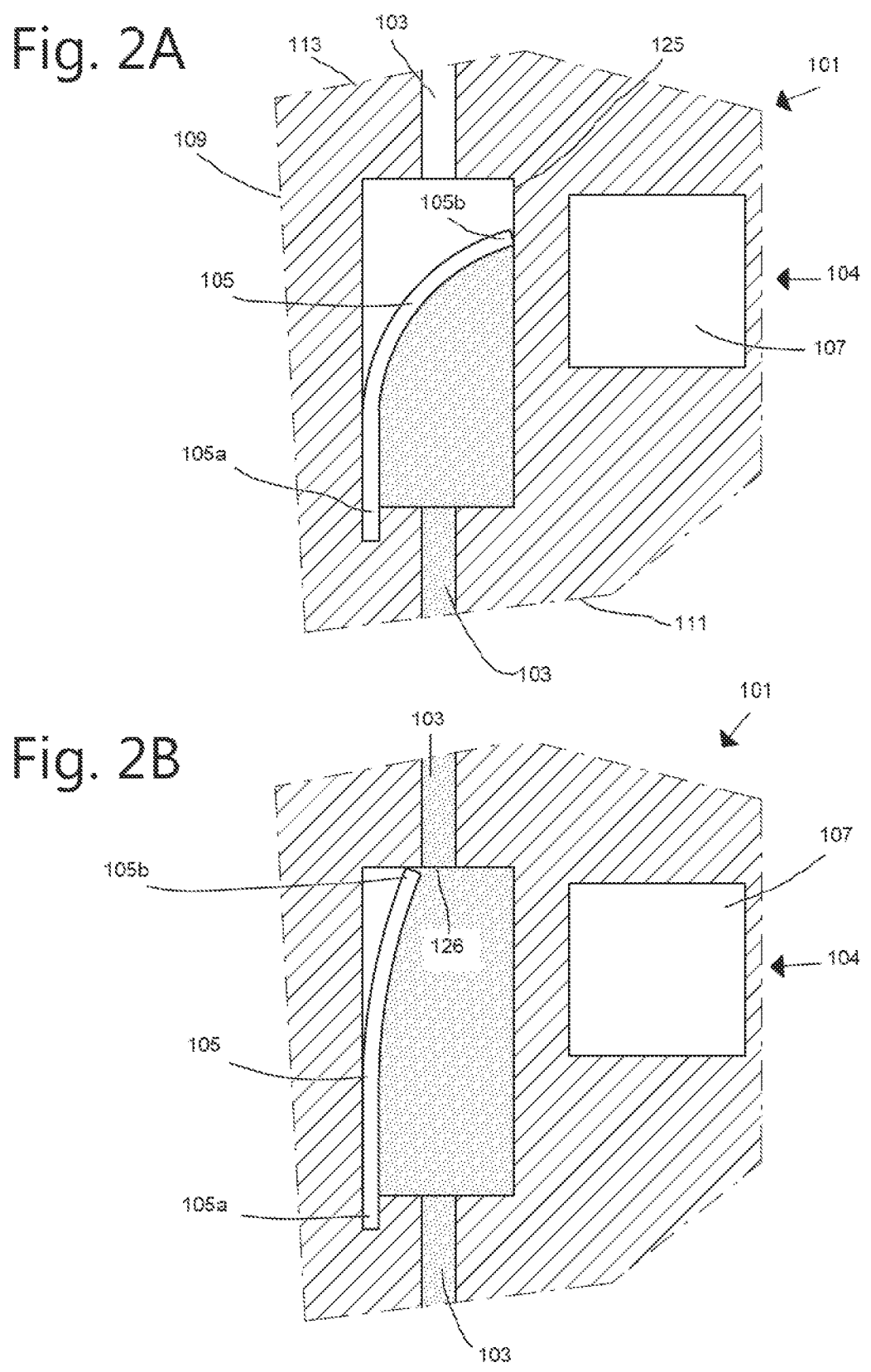

IMPLANTABLE OCULAR DRAINAGE DEVICE FOR CONTROLLING INTRAOCULAR PRESSURE

CROSS-REFERENCE TO RELATED APPLICATIONS

This application is a national phase entry under 35 U.S.C. § 371 of International Patent Application PCT/EP2021/077459, filed Oct. 5, 2021, designating the United States of America and published as International Patent Publication WO 2022/111892 A1 on Jun. 2, 2022, which claims the benefit under Article 8 of the Patent Cooperation Treaty to European Union Patent Application Serial No. 20210723.1, filed Nov. 30, 2020.

TECHNICAL FIELD

The disclosure relates to an implantable ocular drainage device for controlling intraocular pressure comprising at least one drainage channel, and at least one magnetic control mechanism.

BACKGROUND

Glaucoma is an eye disease and is the leading cause of preventable blindness worldwide. A rise in the intraocular pressure (IOP) is considered to be the major risk factor for glaucoma and is associated with an unbalance between the production and drainage of aqueous humor, due to an abnormal increase of resistance to aqueous humor outflow. Glaucoma drainage devices, which are typically hollow tube-like shunts surgically implanted in the eye, provide an alternative pathway through which aqueous humor can effectively drain, thereby lowering IOP in the eye. However, postoperative IOP is unpredictable and conventional shunts often lack in maintaining IOP at an optimal level. The reason behind this is because the drainage of aqueous humor depends on the fixed hydrodynamic resistance of the shunt. In many cases, however, when the postoperative IOP changes, the fixed hydrodynamic resistance of the shunt no longer suffices, which may lead to an undesired high IOP in the eye, when the resistance is too high, or to an undesired over-drainage, if the resistance is too low.

A known magnetically actuated control mechanism for an ocular drainage device is disclosed, for example, in WO2019/051475. This known device comprises a mobile magnetic element, which can be moved by the application of an external magnetic force from a first position, in which the element allows free flow through a drainage tube, to a second position in which the mobile element slows or obstructs flow through the drainage tube. This known device provides a magnetically actuated control mechanism configured to regulate IOP after implanting the ocular drainage device. However, a drawback of the known ocular drainage device is the requirement of at least two stationary magnets in the housing, and a separate movement space for the mobile element.

BRIEF SUMMARY

Provided is an improved implantable ocular drainage device for controlling intraocular pressure and/or a less complex and more compact implantable ocular drainage device comprising a magnetically control mechanism.

The implantable ocular drainage device for controlling intraocular pressure comprises at least one drainage channel, and at least one magnetic control mechanism. The at least one magnetic control mechanism is a magnetic valve mechanism configured to regulate flow in the at least one drainage channel. The magnetic valve mechanism comprises an at least partially moveable magnetic valve element arranged in the at least one drainage channel and, outside the at least one drainage channel, a magnet for providing an attracting magnetic force on the at least partially moveable magnetic valve element to control flow in the drainage channel.

The magnet of the magnetic micro-valve mechanism is arranged or can be positioned close to the drainage channel in which the magnetic valve element of the magnetic micro-valve mechanism is integrated. The at least one magnetic control mechanism only requires one magnet to control the flow through the at least one drainage channel. Hence, it is possible to provide an improved implantable ocular drainage device that can be made relatively compact. In addition, the number of components of the implantable ocular drainage device is relatively low, which makes it possible to provide a less complex device. Further, by using a magnetic valve mechanism, no or less additional space is required in the device for the magnetic valve element, because the at least partially moveable magnetic valve element is arranged in the at least one drainage channel. The magnet provides an attracting force working on the magnetic valve element, such that the at least partially moveable magnetic valve element can be moved under influence of this magnetic attracting force to control flow in the drainage channel. The magnetic micro-valve mechanism will thus help, for example, to prevent or overcome hypotony (low IOP) by enabling to limit or exclude the flow of aqueous humor through the ocular drainage device. Hypotony is, for example, not unusual in the early postoperative period. Then, when the intraocular pressure is rising again, for example, after this initial critical hypotony period is over, the magnetic valve mechanism is configured to promote the flow by moving the magnetic valve element under influence of the attracting magnetic force of the magnet, at least partially, to an at least more open position in order to allow or increase flow through the drainage channel and maintain the intraocular pressure in the eye at a healthy value.

In one aspect, the magnetic valve mechanism is configured to self-regulate flow in the at least one drainage channel, wherein the magnetic valve element is automatically moved in the at least one drainage channel to control flow in the drainage channel depending on the intraocular pressure. The magnetic attracting force of the magnet on the magnetic valve element allows the magnetic valve element and therefore the magnetic valve mechanism to be in an open state or partially open state above a certain pressure threshold, while remaining closed below this pressure. In other words, a passive, self-regulating implantable ocular drainage device is proposed. Such a device uses a magnetic micro-valve mechanism that self-adjusts the flow of aqueous humor through the implant according to the intraocular pressure in the eye. This magnetic valve mechanism does not depend on any external signal for pressure control, i.e., pressure in the drainage channel itself is used as an actuating signal to open or close the drainage channel by means of the magnetic valve element. In addition, this implantable ocular drainage device also comprises minimal components and/or components that require relatively little volume in the device, such that this self-regulating device can also be relatively compact and/or relatively easy to be manufactured. In addition, the magnetic valve element of the self-regulating magnetic valve mechanism can take more than two positions, in contrast to WO2019/051475 in which the magnetic element can only be moved by usage of an external magnetic force between an "on" position or an "off" position, more specific by movement of the mobile element in the movement space toward one of the two predetermined positions close to the stationary magnets. The at least one magnetic valve element of the passive, self-regulating implantable ocular drainage device can be displaced by the intraocular pressure to a maximally open position and a maximally closed position and positions there between. In this way, the passive, self-regulating implantable ocular drainage device can immediately respond to intraocular pressure changes in the eye, so that the intraocular pressure in the eye can be continuously maintained at a healthy value.

In a further aspect, the magnet is adapted to be displaced between predetermined positions with respect to the magnetic valve element for varying the attracting magnetic force on the magnetic valve element. It may be beneficial to adapt or tailor the device to the conditions of the patient by movement of the magnet in the device with respect to the magnetic valve element prior to implanting the device in the patient. After implanting, the magnet is then arranged in the implantable ocular drainage device to provide a constant attracting magnetic force on the magnetic valve element. However, it is also possible that the device is adapted to move the magnetic valve element to another predetermined position after implanting to change the hydrodynamic resistance of the device, for example, if the conditions in the eye after implanting have changed such that an adjustment of the attracting magnetic force on the magnetic valve element is desired. After adjustment by movement of the magnet with respect to the magnetic valve element, the attracting magnetic force on the magnetic valve element will be constant again. It is also possible that the device is equipped with a stationary magnet that cannot be displaced, such that the attracting magnetic force on the magnetic valve element is constant and cannot be changed by displacement of the magnet with respect to the magnetic valve element.

BRIEF DESCRIPTION OF THE DRAWINGS

This disclosure will be explained in more detail below with reference to the appended figures showing exemplary embodiments, in which:

FIGS. 2A-2C show diagrammatic cross-sectional views of a second embodiment of the implantable ocular drainage device;

FIGS. 3A and 3B show diagrammatic top views of a of a third embodiment of the implantable ocular drainage device;

DETAILED DESCRIPTION

Figure 1A:
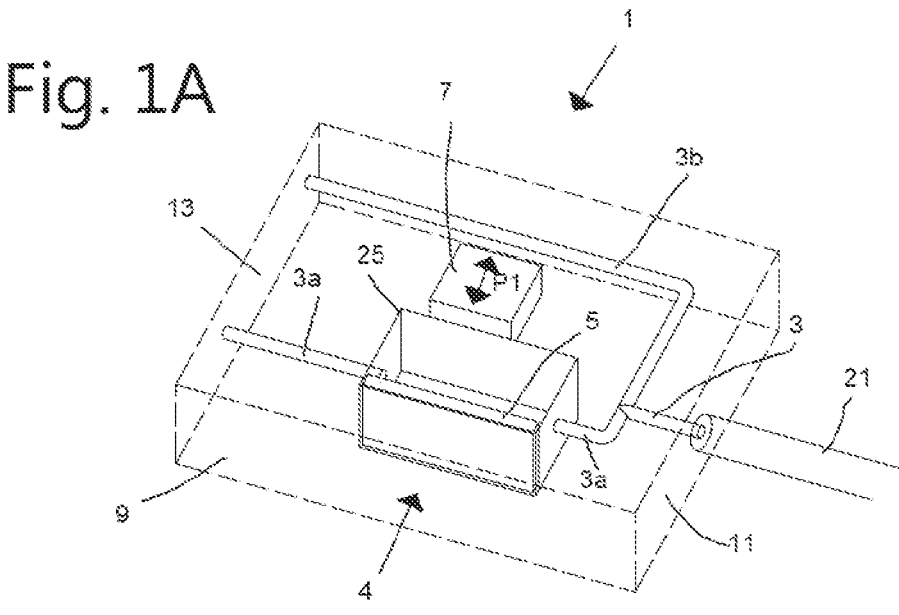
FIGS. 1A and 1B show diagrammatic views of a first embodiment of the implantable ocular drainage device.
Figure 1B:
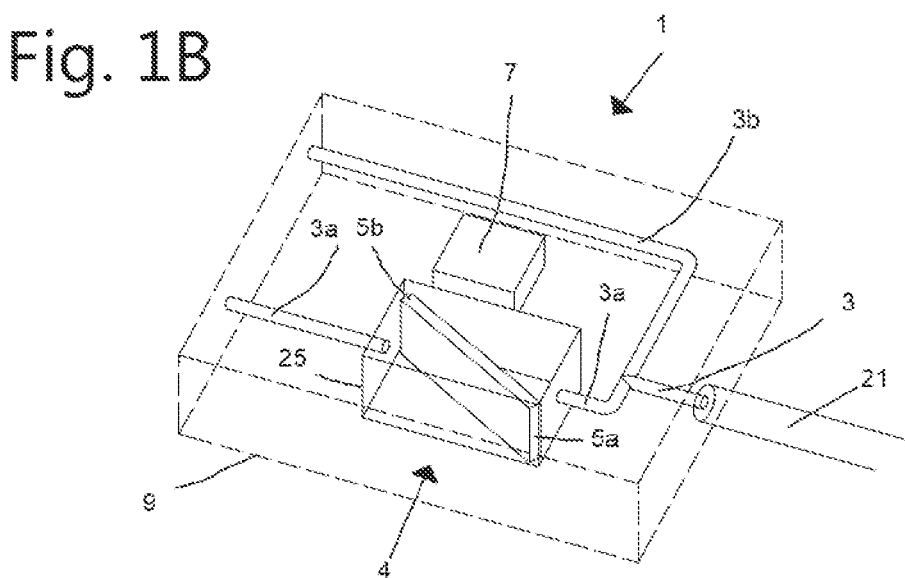

In the following description, identical or corresponding parts have identical or corresponding reference numerals. Each feature disclosed with reference to a specific figure can also be combined with another feature disclosed in this disclosure, unless it is evident for a person skilled in the art that these features are incompatible.

In FIGS. 1A-3B, an implantable ocular drainage device 1; 101; 201; 301; 401 for controlling intraocular pressure is shown. The device 1; 101; 201; 301; 401 comprises a drainage channel 3; 103; 203; 303; 403, and a magnetic control mechanism. The magnetic control mechanism is a magnetic valve mechanism 4; 104; 204; 304; 404 configured to regulate flow in the drainage channel 3; 103; 203; 303; 403. The magnetic valve mechanism 4; 104; 204; 304; 404 comprises an at least partially moveable magnetic valve element 5; 105; 205; 305; 405 arranged in the drainage channel 3; 103; 203; 303; 403 and, outside the drainage channel 3; 103; 203; 303; 403, a magnet 7; 107; 207; 307; 407 for providing an attracting magnetic force on the at least partially moveable magnetic valve element 5; 105; 205; 305; 405 to control flow in the drainage channel 3; 103; 203; 303; 403.

The device 1; 101; 201; 301; 401 further comprises a housing 9; 109; 209; 409 (not shown in FIGS. 4A-4C), wherein the drainage channel 3; 103; 203; 303; 403 extends between an inlet side 11; 111; 211 of the housing 9, 109, 209; 409 and an outlet side of the housing 9; 109; 209. It is possible that the inlet side and the outlet side are the same side of the housing (not shown). In the embodiments shown, the at least one drainage channel 3; 103; 203; 303; 403 is connectable or connected to a drainage tube 21 that, in use, collects aqueous humor from the anterior chamber inside the eye (not shown). In addition, the housing 9, 109, 209; 409 that is diagrammatically sketched in the figures, may in practice have a different geometry, for example, a geometry adapted to the eye or to an efficient implantation procedure (e.g., rounded). The magnetic valve element 5; 105; 205; 305 is located in a chamber 25; 125; 225; 325; 425 having a cross sectional area larger than the drainage channel 3; 103; 203; 303; 403, wherein the chamber 25; 125; 225; 325; 425 is integrated in the drainage channel 3; 103; 203; 303; 403.

Figures 2C, 3A, 3B:
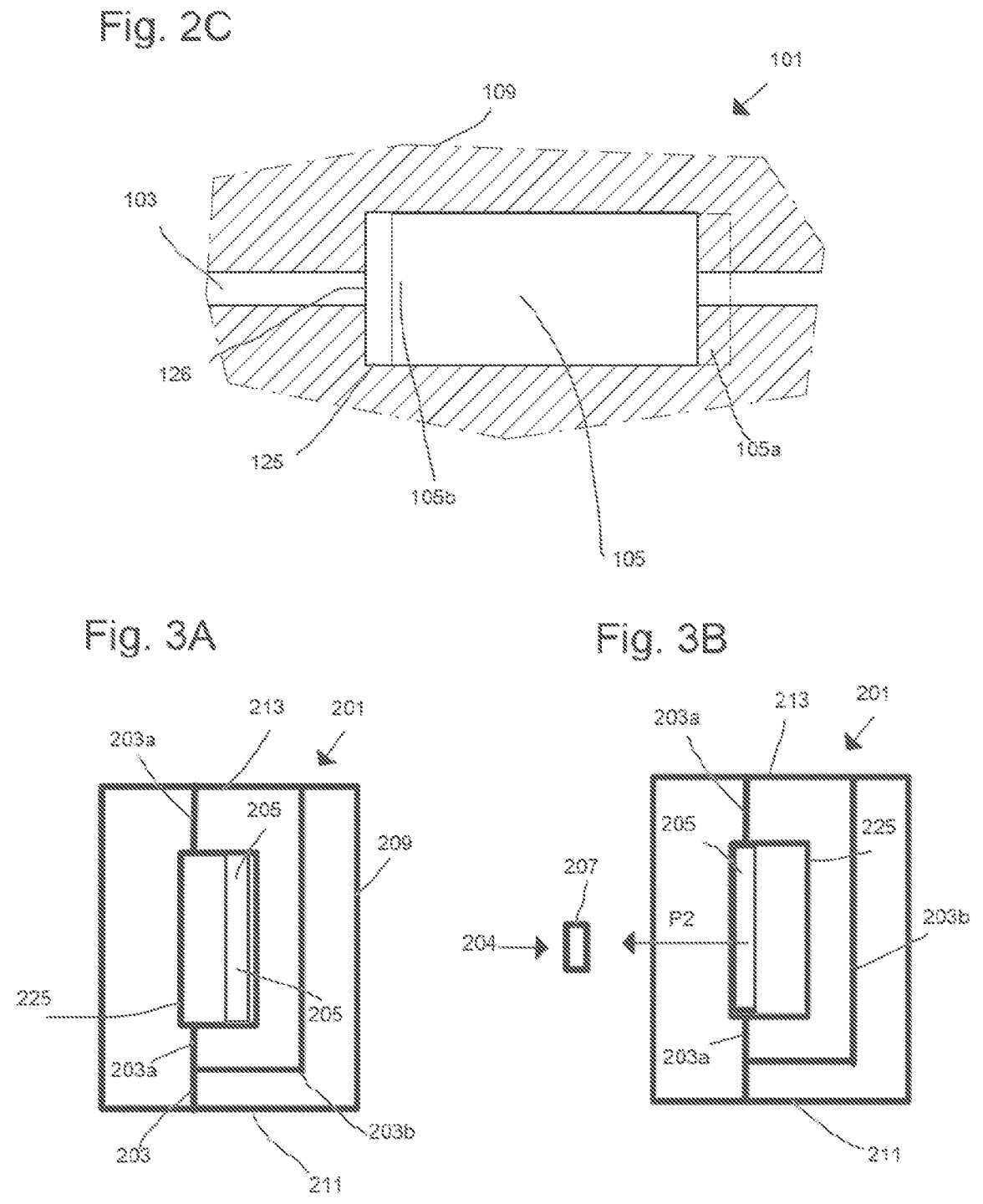

The magnetic valve mechanism 4; 104 shown in FIGS. 1A-2C is configured to self-regulate flow in the at least one drainage channel 3; 103, wherein the magnetic valve element 5; 105 is automatically moved in the chamber 25; 125 forming part of the drainage channel 3; 103 to control flow in the drainage channel depending on the intraocular pressure. The magnetic attracting force of the magnet 7; 107 on the magnetic valve element 5; 105 allows the magnetic valve element 5; 105 to be in an open state or partially open state above a certain pressure threshold, while remaining closed below this pressure. The device 1; 101 uses a magnetic micro-valve mechanism that self-adjusts the flow of aqueous humor through the implant according to the intraocular pressure in the eye. The magnetic valve element 5; 105 can be advantageously displaced by the intraocular pressure to a maximally open position (high IOP) and a maximally closed position (low IOP) and positions there between (medium IOP) to maintain the intraocular pressure in the eye at a healthy value. In the chamber 25; 125 the magnetic valve mechanism 4; 104 is arranged, i.e., the magnet 7; 107 and the chamber 25; 125 containing the magnetic valve element 5; 105 are located in the housing 9; 109. The magnetic valve element 5; 105 is or comprises a partially moveable flap located in the chamber 25, 125 forming part of the drainage channel 3; 103. The flap is adapted to provide more respectively less flow through the drainage channel if the intraocular pressure rises respectively falls. One side 5a; 105a of the flap is immovable fixated whereas an opposite side 5b; 105b of the flap can be moved for opening or closing the drainage channel 3; 103 to regulate flow there through. The side 5a of the flap shown in FIGS. 1A and 1B is connected to the chamber 25 in a pivotable manner, such that the opposite side 5b can move to a closed position (FIG. 1B) or to an open position (FIG. 1A) depending on the intraocular pressure. The side 105a of the flap shown in FIGS. 2A and 2B is immovably fixed to a wall of the chamber 25, such that the opposite side section 5*b* can move by bending to a closed position (FIG. 2A) or to an open position (FIG. 2B) depending on the intraocular pressure. As a result of the diagrammatically sketched FIGS. 1A-2C it will be difficult to observe that the valve elements 5; 105 can also take positions between a closed and open chamber 25, but these devices 1, 101 are capable to deal with a medium pressure, i.e., medium IOP, for example, by closing chamber outlet 126 (FIG. 2B) partially by the valve element 105 or by using more than one chamber outlet (not shown), which can be opened or closed independently from each other by a valve element. It is noted that FIG. 2C shows a cross-section of the device 101 from a different side than FIGS. 2A and 2B, wherein the valve element 105 is shown in a position close to the closed position of the valve element 105 shown in FIG. 2A. In the not fully closed position of the valve element 105 of FIG. 2C, flow will take place through the drainage channel 103 between the inlet side 111 and the outlet side 113 of the housing 109, but this flow will be a decreased flow through the drainage channel 103 compared to the flow with the valve element 105 in a more open position such as, for example, shown in FIG. 2B.

The permanent magnet 7 of the device 1 (FIGS. 1A and 1B) can be displaced (indicated with arrows P1) between predetermined positions (not shown) with respect to the magnetic valve element 5 for varying the attracting magnetic force on the magnetic valve element 5. The magnet 7 can be displaced to tailor or tune the attracting magnetic force on the magnetic valve element 5 to the specific conditions of the patient. After implanting the device 1 in the patient, the magnet 7 is then arranged in the device 1 to provide a constant attracting magnetic force on the magnetic valve element 5. However, it is also possible to re-configure the device 1 after implanting by movement of the permanent magnet 7 to another predetermined position to change the hydrodynamic resistance of the device 1, for example, the permanent magnet 7 can be non-invasively displaced in the housing 9 as indicated by arrow P1 by using an externally provided magnetic field (not shown). After this reconfiguration, the attracting magnetic force on the magnetic valve element will be constant again. The device 101 (FIGS. 2A-2C) is equipped with a stationary permanent magnet 107 that cannot be displaced, such that the attracting magnetic force on the magnetic valve element 105 is constant. In addition to or instead of changing distance of the magnetic valve element 5; 105 to the magnet 7; 107, it is also possible to adapt the dimensions of the magnetic valve element 5; 105 to obtain a desired pressure threshold of the magnetic valve element 5; 105 tailored to the individual patient.

In the device 1; 201, the drainage channel 3; 203 is subdivided into a primary channel 3*a*; 203*a* and a secondary channel 3*b*; 203*b* inside the housing 9; 109, wherein the primary channel 3*a*; 203*a* and the secondary channel 3*b*; 203*b* define flow paths of the drainage channel 3; 203 inside the housing 9; 109. In at least one of the primary channel 3*a*; 203*a* and the secondary channel 3*b*; 203*b* the magnetic valve element 5; 205 is arranged. In the devices 1; 201 the magnetic valve element 5; 205 is arranged in the chamber 25; 225 forming part of the primary channel 3*a*; 203*a*. The secondary channel 3*b*; 203*b* without the magnetic valve element is permanently open, preferably the secondary channel 3*b*; 203*b* has a cross sectional area smaller (not shown) than the primary channel 3*a*; 203*a* with the magnetic valve element 5; 205. The secondary outlet channel 3*b*; 203*b* having a cross-sectional area smaller than the primary outlet channel 3*a*; 203*a* remains open in both "low flow" or "high flow" modes of the device 1; 201. The dimensions of the secondary outlet channel 3*b*; 203*b* have been predetermined in order to achieve a desired minimum drainage, i.e., the device 1; 201 is in the "low flow" mode. It is also possible to include a magnetic valve element (not shown) in the secondary outlet channel that may be configured to remain longer open than the magnetic valve element in the primary outlet channel.

The presence of multiple magnetic valve mechanisms in the devices 1; 101; 201 is not shown, but is possible. Multiple magnetic valve mechanisms in multiple drainage channels in an implantable ocular drainage device will allow for the control of a wider range of pressures, as multiple drainage channels can be, for example, simultaneously open at the same time to allow for more aqueous humor to leave the anterior chamber, thus significantly reducing a relatively high intraocular pressure in the eye. Further, when applying multiple self-regulating magnetic valve mechanisms in a device (not shown), it is possible to use a different magnetic attracting force on a first magnetic valve element than on a second magnetic valve element, such that the first and second magnetic valve elements open/close at different pressure thresholds. Further, it is possible that multiple valves in one implantable ocular drainage device (not shown) can be operated independently with different magnetic field orientations. In a device provided with more than two valves many combinations with the valves (open or closed position) are possible to control the flow in the drainage channel (or channels). In addition, it is possible in the device 101 to subdivide the drainage channel 103 into a primary channel and a secondary channel inside the housing, instead of using an un-subdivided drainage channel 103 as shown in FIGS. 2A-2C.

In the device 201 shown in FIGS. 3A and 3B, the magnetic valve element 205 of the magnetic valve mechanism 204 is a magnetic valve block. This magnetic valve block is completely moveable by positioning or activating a magnet 207 on the left or on the right side of the housing 209. The magnet 207 and its magnetic field will move the magnetic valve block from the open position shown in FIG. 3A to the closed position shown in FIG. 3B, for example, as shown in FIG. 3B by arrow P2. The open position allows flow through the primary channel 203*a* of the drainage channel 203 and the closed position obstructs flow through the primary channel 203*a* of the drainage channel 203.

In this document, two different valve mechanisms—active 204; 304; 404 and passive 4; 104—are disclosed for an implantable ocular drainage device. The active, magnetically adjustable device 201; 301; 401 is comprised of a drainage channel 203 containing the magnetic microvalve(s) and a housing 209; 409. After implantation of the device 201, the aqueous humor enters the drainage channel 203, which is further subdivided into primary 203*a* and secondary 203*b* outlet channels. In the primary channel 203*a*, an actuation chamber 225 with the micro-valve magnetic element 205 in the form of a rectangular valve block is arranged. The magnetic valve element 205 and the chamber 225 are not restricted to a rectangular shape and may have any shape as long as it is possible to open and close the primary channel 203*a* by means of a magnetic valve element. An external magnet 207 may be used to move this magnetic valve element 205 to the "closed" or "open" positions: (i) when closed, the device 201 is in a "low flow" mode where the hydrodynamic resistance reaches its maximum; (ii) when open, the device 201 is in a "high flow" mode with its hydrodynamic resistance at a minimum. In the case of an active device 201, the magnetic valve element 205 should normally be switched to and maintained in the closed state ("low flow" mode) in the early post-surgical period to prevent hypotony. Then, when this initial critical period is over and the doctor determines that the pressure is rising again, the magnetic valve element 205 can be switched by using the magnet 207 (to be positioned on an opposite side of the device 201 than shown in FIG. 3B) to the open position in order to increase flow and maintain the IOP at a healthy value. The fluid flow through the device 201 is thus easily modulated by the ophthalmologist by simply moving an external magnet 207 close to the eye and in the desired direction, depending on whether the valve is to be opened or closed. The external magnet 207 may be a specifically designed instrument that can generate a particular magnetic field, e.g., generated by an electromagnet.

It is also possible to arrange the micro-valve element directly in the at least one drainage channel without using a chamber shown in the figures.

Figure 4A:
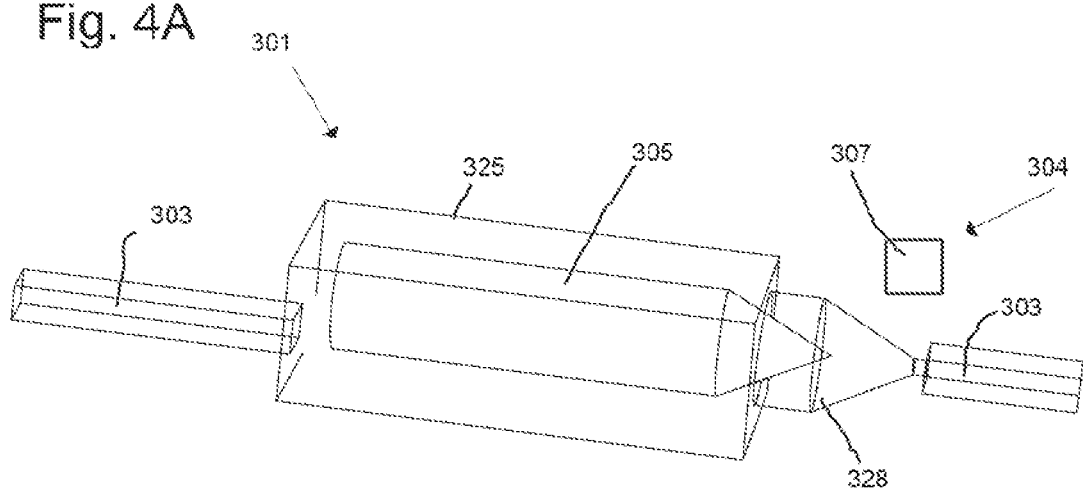
FIGS. 4A-4C show diagrammatic views of a of a fourth embodiment of the implantable ocular drainage device.
Figure 4B:
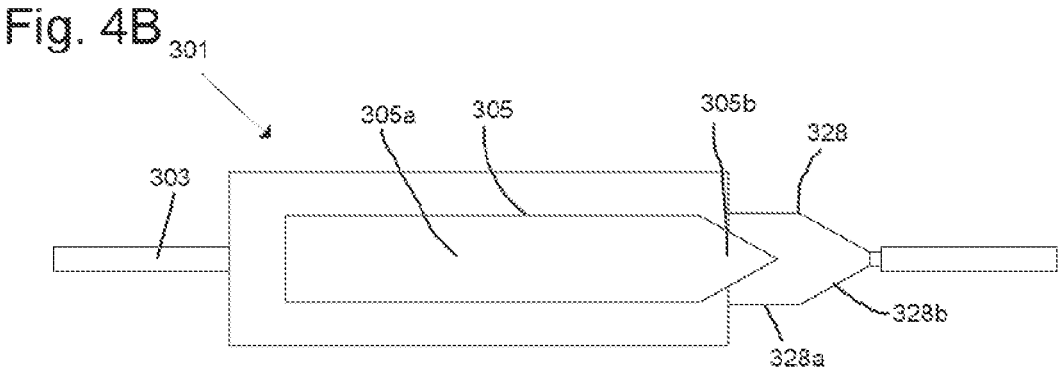
Figure 4C:
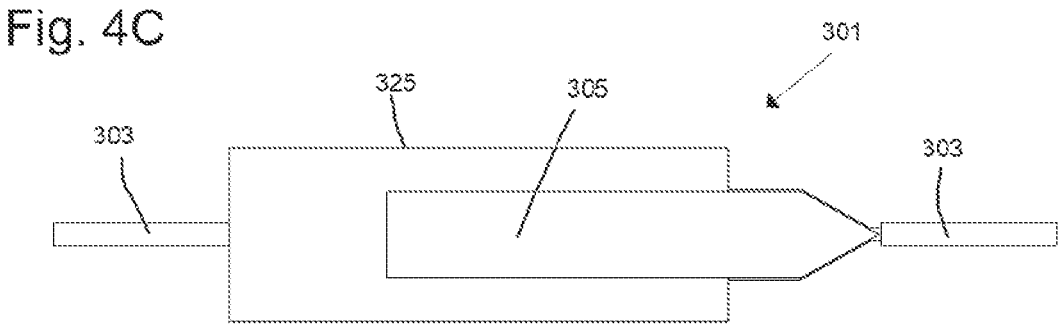

In the device 301 shown in FIGS. 4A-4C, the magnetic valve element 305 has a pencil-like design, i.e., a main body section 305a and a male end section 305b. The male end section 305b is a conical-shaped projection formed integrally with main body section 305a. The device 301 comprises a female section or receiving portion 328 for receiving a portion of the magnetic valve element 305. The receiving portion 328 is adapted to receive the male end section 305b. In the embodiment shown in FIGS. 4A-4C, the receiving portion 328 is adapted to receive the male end section 305b and a portion of the main body section 305a close to the male end section 305b, i.e., the receiving portion 328 has a first receiving portion section 328a and a second receiving portion section 328b. The first receiving portion section 328a is complementary in shape and size to the portion of the main body section 305a close to the male end section 305b. The main body section 305a close to the male end section 305b may be, for example, cylindrical. The second receiving portion section 328b is complementary in shape and size to the male end section 305b. As shown the receiving portion 328 is provided by a projection from an end wall of the chamber 325. By means of the pencil design, the magnetic valve element 305 can be moved in a relatively reliable and stable manner by means of the external magnet 307 between a closed position (FIG. 4C) and an open position (FIG. 4B) and vice versa or into a position (not shown) between the open and closed position.

FIGS. 5A-5D show another embodiment of an implantable ocular drainage device 401. The device 401 comprises an active valve mechanism 404 (FIG. 5B), i.e., a rotatable magnetic valve element 405 and an external magnet 407.

The housing 409 is provided with central cut-out 425 for receiving the rotatable magnetic valve element 405.

Figure 5A:
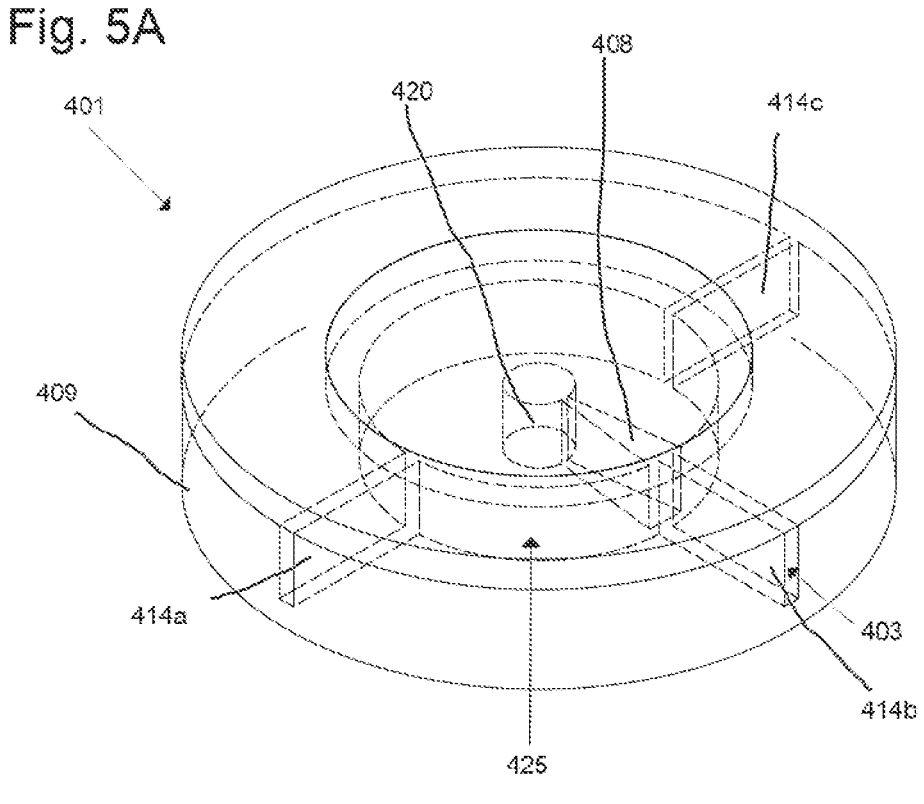
FIGS. 5A-5D show diagrammatic views of a of a fifth embodiment of the implantable ocular drainage device.
Figure 5B:
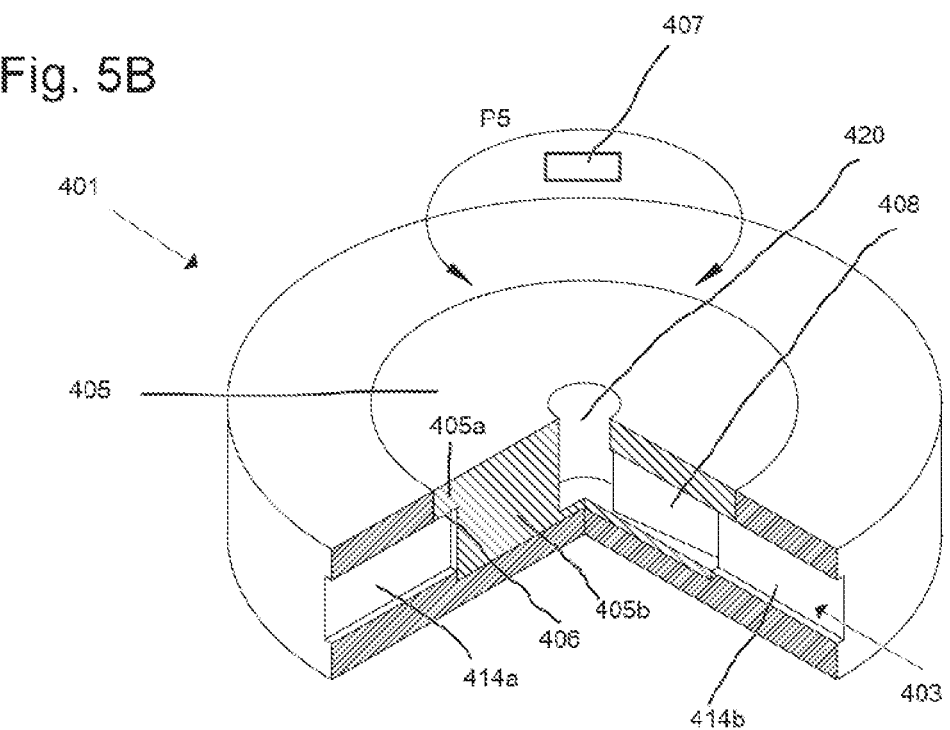

The magnetic valve element 405 has a mushroom shape as can be seen in FIGS. 5A and 5B, i.e., a head portion 405a and a stem portion 405b. The head portion 405a and the stem portion 405b are cylindrical, wherein the stem portion 405b has a diameter smaller than the head portion 405a. The head portion 405a and the stem portion 405b are supported by the housing 409 in a rotatable manner, in particular, by means of the head portion 405a bearing on an internal edge 406 of the housing 409. Such a mushroom design facilitates an accurate, stable and reliable rotational movement of the magnetic valve element 405 when using the external magnet 407. The head portion 405a (larger diameter) allows this part of the element to partially rest on top of housing channels to be discussed below, stabilizing the element 405 in its position as well as blocking unwanted flow from the closed microfluidic housing channels.

The core of the magnetic valve element 405 is hollow and forms a channel chamber 420 from bottom to the top. The channel chamber 420 is in fluid communication with an internal channel 408 of the magnetic valve element 405. A center line of the channel chamber 420 (coinciding with the center line of the device 401) coincides with the rotation axis of the rotatable magnetic valve element 405. Seen from this rotation axis, the internal channel 408 extends radially outwardly from the channel chamber 420. The internal channel 408 as shown has a wedge-shape, wherein the cross section of the internal channel 408 increases in a direction away from the channel chamber 420.

The portion of the housing 409 surrounding the cut-out 425 for receiving the magnetic valve element 405 comprises multiple housing channels 414a-414c that have different dimensions, resulting in different outflow resistances. The housing 409 may further be provided with a disc-like lid (not shown) positioned on top of the magnetic valve element 405 and the surrounding housing portion shown in FIGS. 5A and 5B. The disc-like lid may be provided with a drainage hole that provides the outlet side of the housing 409. The drainage channel 403 extends between this drainage hole and one of the outer (radially seen with respect to the rotation axis) ends of the housing channels 414a-414c.

Figure 5C:
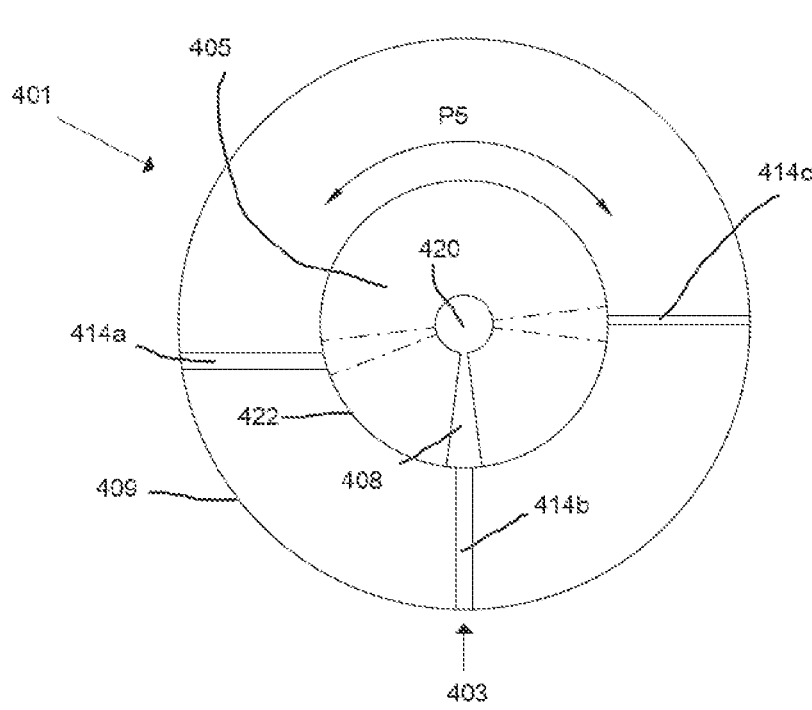
Figure 5D:
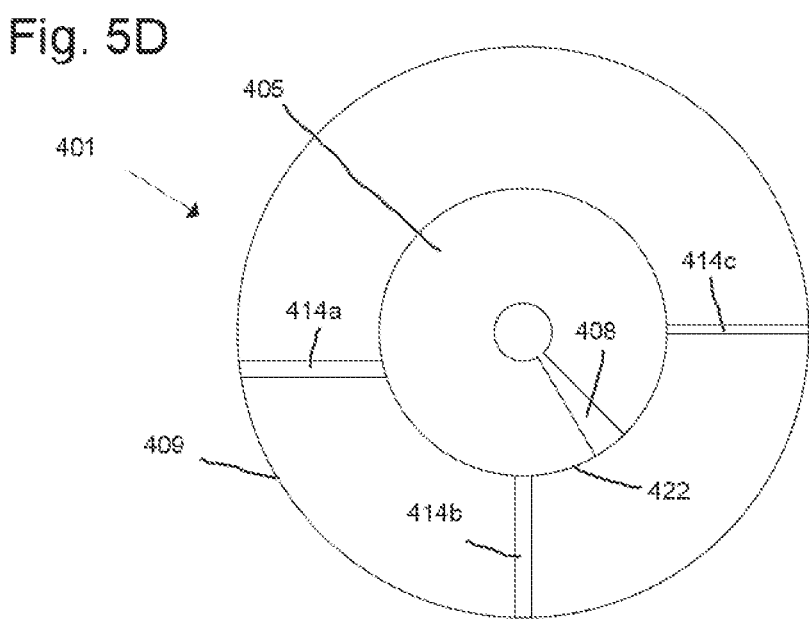

Upon rotation of the magnetic valve element 405 in one of the directions indicated by double-arrow P5, the internal channel 408 can be positioned toward an opening of one of the housing channels 414a-414c in an open position (FIGS. 5A-5C) or in an at least partly open position (not shown), or it can be positioned toward an inner wall 422 (FIG. 5D) of the housing 409 in a closed position. The primary function of the rotatable magnetic valve element 405 is to either open a housing channel 414a-414c and thereby allowing drainage, or to close it and thereby restricting drainage from the implant. When positioned toward the opening of one of the housing channels 414a-414c, for example, housing channel 414b as shown in FIGS. 5A-5C, fluid flowing through this housing channel can flow, via the internal channel 408 and the channel chamber 420 toward its outlet at the top and out of the implantable ocular drainage device 401. The secondary function of the magnetic valve element 405 may be to select which of the housing channels 414a-414c to open, for example, flow communication between internal channel 408 and channel 414a (dotted lines indicating internal channel 408 in FIG. 5C) provides high drainage, between internal channel 408 (see FIG. 5C) and channel 414b provides medium drainage, and/or between internal channel 408 and channel 414c (dotted lines indicating internal channel 408 in FIG. 5C) provides low drainage. No drainage can be provided if the internal channel 408 is positioned toward an inner wall 422 (FIG. 5D) of the housing 409 as mentioned above.

The outer ends of the housing channels 414a-414c may be connected by tubes with a ring (not shown) surrounding the device 401, wherein aqueous humor is drained from the anterior chamber, via a tube, into the ring and the device 401.

In the embodiment of the implantable ocular drainage device 401 shown in the figures, the device 401 comprises three housing channels 414a-414c, but is also possible to provide more or less housing channels. It is also possible to provide a single housing channel, wherein flow can be controlled by alignment of the internal channel 408 of the rotatable magnetic valve element 405 with respect to the opening of the single housing channel. In such an embodiment "full" alignment between the internal channel 408 and the opening of the single housing channel means maximum flow between the internal channel and the single housing channel, wherein rotation into "half" alignment or a position between "half" and "full" alignment means a reduced flow between the internal channel and the single housing channel with respect to the maximum flow. Again, no drainage/flow can be provided if the internal channel 408 is positioned toward an inner wall 422 of the housing 409 as mentioned above.

The invention claimed is:

1. An implantable ocular drainage device for controlling intraocular pressure comprising at least one drainage channel, and at least one magnetic control mechanism, wherein the at least one magnetic control mechanism is a magnetic valve mechanism configured to regulate flow in the at least one drainage channel, wherein the magnetic valve mechanism comprises an at least partially moveable magnetic valve element arranged in the at least one drainage channel and, outside the at least one drainage channel, a magnet for providing an attracting magnetic force on the at least partially moveable magnetic valve element to control flow in the drainage channel, wherein the magnet is adapted to be displaced between predetermined positions with respect to the magnetic valve element for varying the attracting magnetic force on the magnetic valve element.

2. The device according to claim 1, wherein the implantable ocular drainage device comprises a housing, wherein the at least one drainage channel extends between an inlet side of the housing and an outlet side of the housing.

3. The device according to claim 2, wherein in the housing at least one magnetic valve mechanism is arranged.

4. The device according to claim 1, wherein the at least one drainage channel is connectable or connected to a drainage tube that, in use, collects aqueous humor from the anterior chamber inside the eye.

5. An implantable ocular drainage device for controlling intraocular pressure comprising at least one drainage channel, and at least one magnetic control mechanism, wherein the at least one magnetic control mechanism is a magnetic valve mechanism configured to regulate flow in the at least one drainage channel, wherein the magnetic valve mechanism comprises a rotatable magnetic valve element arranged in a housing and fluidically coupled to the at least one drainage channel, wherein the rotatable magnetic valve element has a hollow core forming a channel chamber from bottom to top, wherein the channel chamber is in fluid communication with an internal channel of the rotatable magnetic valve element, wherein the internal channel extends radially outwardly from the channel chamber, and an external magnet positioned outside the housing for providing an attracting magnetic force on the rotatable magnetic valve element to selectively control flow in the drainage channel by rotating the rotatable magnetic valve element in one of two rotation directions.

6. The device of claim 5, wherein the magnet is adapted to be displaced between predetermined positions with respect to the magnetic valve element for varying the attracting magnetic force on the magnetic valve element.

7. The device of claim 5, wherein the implantable ocular drainage device comprises the housing, wherein the at least one drainage channel extends between an inlet side of the housing and an outlet side of the housing.

8. The device of claim 5, wherein upon rotation of the magnetic valve element in one of the two rotation directions, the internal channel of the magnetic valve element is rotated to be positioned towards an opening of one of a plurality of housing channels of the housing in an open position or in an at least partly open position, or is positioned towards an inner wall of the housing in a closed position.

9. The device of claim 5, wherein upon rotation of the magnetic valve element in one of the two rotation directions, the internal channel of the magnetic valve element is rotated to be positioned towards an opening of a single housing channel of the housing in an open position or in an at least partly open position, or is positioned towards an inner wall of the housing in a closed position.

10. The device of claim 7, wherein in the housing the at least one magnetic valve mechanism is arranged.

11. The device of claim 7, wherein the housing is provided with a central cut-out configured to receive the rotatable magnetic valve element.

12. The device of claim 11, wherein the magnetic valve element has a mushroom shape with a head portion and a stem portion, wherein the head portion and the stem portion are cylindrical, wherein the stem portion has a diameter smaller than the head portion, and wherein the head portion and the stem portion are supported by the housing in a rotatable manner.

13. The device of claim 5, wherein the at least one drainage channel is connectable or connected to a drainage tube which in use collects aqueous humor from the anterior chamber inside the eye.

14. The device of claim 7, wherein inside the housing the at least one drainage channel is subdivided into a primary channel and a secondary channel, wherein the primary channel and the secondary channel define flow paths of the at least one drainage channel inside the housing.

* * * * *